(12) United States Patent
Goumas

(10) Patent No.: US 8,043,241 B2
(45) Date of Patent: Oct. 25, 2011

(54) CONVERTIBLE SUPPORT SYSTEM, DEVICE, AND METHOD FOR SHOULDER SURGERY PATIENTS

(75) Inventor: Douglas Goumas, Bedford, NH (US)

(73) Assignee: G Force Braces, LLC, Bedford, NH (US)

(*) Notice: Subject to any disclaimer, the term of this patent is extended or adjusted under 35 U.S.C. 154(b) by 289 days.

(21) Appl. No.: 12/424,805

(22) Filed: Apr. 16, 2009

(65) Prior Publication Data

US 2010/0121236 A1    May 13, 2010

Related U.S. Application Data

(60) Provisional application No. 61/199,094, filed on Nov. 12, 2008.

(51) Int. Cl.
*A61F 5/00* (2006.01)
*A61F 5/37* (2006.01)

(52) U.S. Cl. ........... 602/4; 602/20; 602/21; 128/845; 128/846; 128/878; 128/892; 5/621; 5/623; 5/646; 5/647; 5/733

(58) Field of Classification Search .......... 602/4, 19–21; 128/845, 846, 869, 870, 878, 881, 892; 5/621–623, 5/646, 647, 729, 733
See application file for complete search history.

(56) References Cited

U.S. PATENT DOCUMENTS

| | | |
|---|---|---|
| D247,311 S | 2/1978 | Carter |
| 4,173,048 A | 11/1979 | Varaney |
| 4,186,738 A | 2/1980 | Schleicher et al. |
| 4,210,317 A | 7/1980 | Spann et al. |
| 4,270,235 A | 6/1981 | Gutmann |
| 4,375,809 A | 3/1983 | Meals |
| D287,641 S | 1/1987 | Schaefer |
| D296,932 S | 7/1988 | Tranghese |
| 4,896,660 A | 1/1990 | Scott |
| D321,562 S | 11/1991 | Ljungvall |
| 5,418,991 A * | 5/1995 | Shiflett ............... 5/650 |
| D362,072 S | 9/1995 | Sternberg |
| 5,584,303 A | 12/1996 | Walle |
| 5,603,692 A | 2/1997 | Maxwell |
| D382,057 S | 8/1997 | Swedberg et al. |
| 5,716,334 A | 2/1998 | Wade |
| D396,291 S | 7/1998 | Bakes |
| 5,782,244 A * | 7/1998 | Kostich .............. 128/869 |
| D413,982 S | 9/1999 | Swedberg et al. |
| D415,281 S | 10/1999 | Swedberg et al. |
| D422,362 S | 4/2000 | Ames |

(Continued)

*Primary Examiner* — Patricia Bianco
*Assistant Examiner* — Keri Nelson
(74) *Attorney, Agent, or Firm* — Lipsitz & McAllister, LLC

(57) ABSTRACT

A support system for surgical patients, a convertible support for surgical patients, and a method for providing a convertible support for surgical patients is provided. The support system includes an arm cradle adapted to hold an arm of a patient at an angle when the patient is in a supine position and a side bolster adapted to be positioned against a side of a patient opposite the arm cradle. The side bolster is adapted to stabilize the patient in the supine position. The arm cradle is adapted to hold an arm of a patient at an angle conducive to recovery from shoulder surgery when the patient is in a supine position. The arm cradle is also adapted to be worn as a sling when the patient is ambulatory. The arm cradle, side bolster, and an optional head support may be secured to a mat in a temporary manner.

21 Claims, 4 Drawing Sheets

U.S. PATENT DOCUMENTS

| | | |
|---|---|---|
| 6,047,420 A | 4/2000 | Priester, III et al. |
| D426,307 S | 6/2000 | Swedberg et al. |
| D447,568 S | 9/2001 | Hall et al. |
| D475,757 S | 6/2003 | Silverman et al. |
| 6,691,353 B2 | 2/2004 | Fuhriman |
| 7,017,215 B1 | 3/2006 | Singer et al. |
| 7,189,213 B1 * | 3/2007 | Weber .............................. 602/20 |
| 7,244,239 B2 * | 7/2007 | Howard ............................. 602/4 |
| 7,441,293 B1 | 10/2008 | Singer et al. |
| D624,344 S | 9/2010 | Kashey |

* cited by examiner

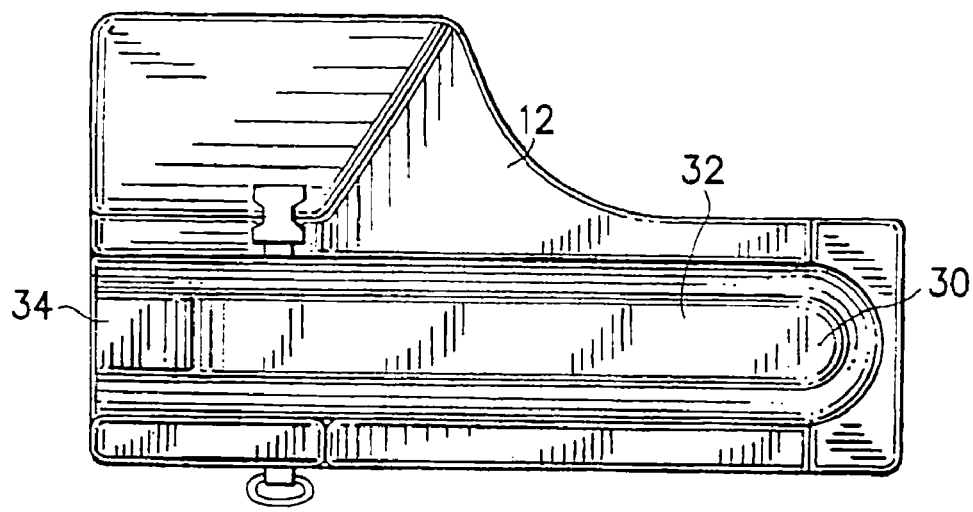
FIG.5
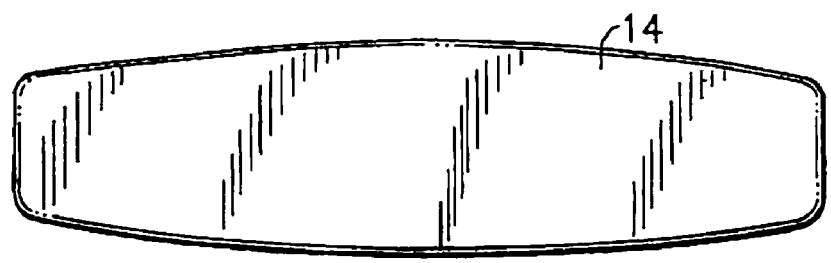
FIG.6
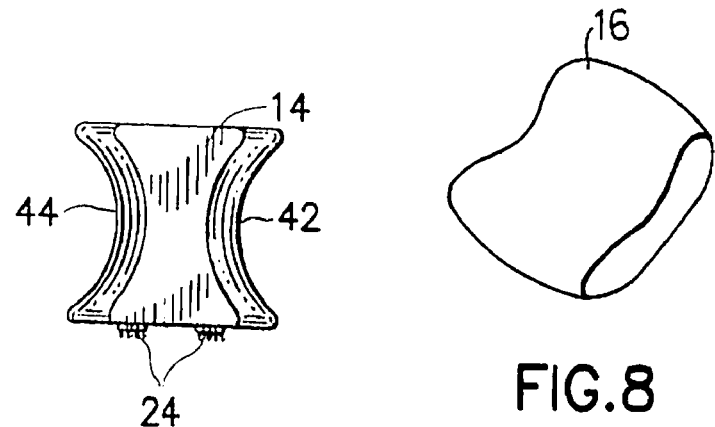
FIG.7
FIG.8

CONVERTIBLE SUPPORT SYSTEM, DEVICE, AND METHOD FOR SHOULDER SURGERY PATIENTS

This application claims the benefit of U.S. provisional patent application No. 61/199,094 filed on Nov. 12, 2008, which is incorporated herein and made a part hereof by reference.

BACKGROUND OF THE INVENTION

The present invention relates to supports for patients recovering from shoulder surgery. More specifically, the present invention relates to systems, apparatus, and methods that provide support for a patient's arm which enables shoulder surgery patients to sleep in a supine position in a stable manner and which include a cradle portion adapted to be worn as a sling during waking hours.

The prior art discloses several types of support pillows for shoulder surgery patients. However, none of the prior art devices provide support for the surgically repaired arm and shoulder while at the same time restricting patient movement (e.g., rolling over or shifting onto one side) in order to prevent injury or damage to the surgically repaired shoulder during sleep. Further, none of the prior art support pillows are convertible into a sling for use by the patient during waking hours.

Accordingly, it would be advantageous to provide a support device for shoulder surgery patients that supports the surgically repaired shoulder and arm while at the same time restricting patient movement. It would also be advantageous if a portion of such a support device could be adapted to be worn as a sling during waking hours.

The systems, methods and apparatus of the present invention provide the foregoing and other advantages.

SUMMARY OF INVENTION

The present invention relates to a support system for surgical patients, a convertible support for surgical patients, and a method for providing a convertible support for surgical patients.

In one example embodiment, a support system for surgical patients is provided. The support system comprises an arm cradle adapted to hold a first arm of a patient at an angle when the patient is in a supine position and a side bolster with a first side adapted to be positioned against a side of a patient opposite the arm cradle. The side bolster is adapted to stabilize the patient in the supine position.

The support system may further comprise a mat. The mat may be positioned on a bed, the floor, or other flat surface adapted for sleeping. The arm cradle and the side bolster may be temporarily secured to the mat. In addition, a T-shaped strap may be provided for securing the arm cradle to the mat and the patient. The T-shaped strap may comprise a first end adapted to be secured to the arm cradle, a first length of strap for encircling a waist of the patient, and a second length of strap adapted to be secured to the mat which is attached to the first length and perpendicular to the first length.

The support system may also comprise a head support secured to the mat and adapted to support a head of the patient.

In a further example embodiment, the arm cradle may comprise a first section adapted to accept an upper arm of the patient, and a second section adapted to accept a lower arm of the patient. The arm cradle may further comprise a base portion. The first section may be angled with respect to the base portion and the second section may be angled with respect to the first section. For example, the first section may be at an angle in a first range between 0 and 30 degrees with respect to the base portion and the second section may be at an angle in a second range between 90 and 170 degrees with respect to the first section.

In another example embodiment, the angle between the first section and the base portion may be adjustable within the first range and the angle between the second section and the first section may be adjustable within the second range.

The arm cradle may also comprise a third section adapted to support a hand of the patient. The third section may be angled with respect to the second section. For example, the third section may be at an angle in a third range between 120 and 150 degrees with respect to the second section. The angle between the third section and the second section may be adjustable within the third range.

In addition, one or more straps may be fixed to the arm cradle for securing the first arm of the patient in the arm cradle.

In a further example embodiment, the arm cradle may be adapted to be worn as a sling when the patient is ambulatory. In such an embodiment, one or more straps may be affixed to the arm cradle and configured to support the arm cradle for use as a sling. For example, the one or more straps may comprise a shoulder strap and a waist strap. Additionally, the one or more straps may be adapted to secure the arm cradle to the mat when the patient is in the supine position.

The side bolster may have a second side adapted to conform to a second arm of the patient in an extension position. The side bolster may have a second side which is symmetrical with the first side, enabling use of the side bolster on either side of a patient. At least portions of the first side and the second side of the side bolster may be concave.

The patient may comprise a shoulder surgery patient. The angle at which the arm cradle holds the first arm of the patient in the supine position may be chosen so as to speed recovery from the shoulder surgery while immobilizing the shoulder during sleep.

The present invention also provided a convertible support for shoulder surgery patients. In one example embodiment, the convertible support may comprise an arm cradle which is adapted to hold an arm of a patient at an angle when the patient is in a supine position and adapted to be worn as a sling when the patient is ambulatory. Straps affixed to the arm cradle may be configured to support the sling when the patient is ambulatory. The arm cradle of the convertible support may include additional features as discussed above in connection with the support system.

The present invention also includes a method for providing a convertible support system for shoulder surgery patients. In one example embodiment, the method may comprise providing an arm cradle adapted to hold a first arm of a patient at an angle when the patient is in a supine position and adapted to be worn as a sling when the patient is ambulatory, as well as providing straps affixed to the arm cradle configured to support the sling when the patient is ambulatory. The method may further comprise providing a side bolster with a first side adapted to be positioned against a side of a patient opposite the arm cradle, where the side bolster adapted to stabilize the patient in the supine position. The method may include providing additional features and elements discussed above in connection with the support system.

BRIEF DESCRIPTION OF THE DRAWINGS

The present invention will hereinafter be described in conjunction with the appended drawing figures, wherein like reference numerals denote like elements, and:

FIG. 5 shows a top plan view of an example embodiment of an arm cradle in accordance with the present invention;

FIG. 6 shows a top plan view of an example embodiment of a side bolster in accordance with the present invention;

FIG. 7 shows a front elevational view of an example embodiment of a side bolster in accordance with the present invention; and FIG. 8 shows an example embodiment of an optional head support in accordance with the present invention.

DETAILED DESCRIPTION

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing an embodiment of the invention. It should be understood that various changes may be made in the function and arrangement of elements without departing from the spirit and scope of the invention as set forth in the appended claims.

The present invention relates to a support system for surgical patients, a convertible support for surgical patients, and a method for providing a convertible support for surgical patients. While the present invention is described in detail below in connection with shoulder surgery patients, those skilled in the art will appreciate that the present invention may be used (or easily adapted for use) with patients recovering from other types of surgeries and/or injuries, such as upper arm surgeries or injuries, lower arm surgeries or injuries, elbow surgeries or injuries, hand surgeries or injuries, shoulder injuries, and any other injuries or surgeries that would require a patient to use a sling and to remain immobilized while sleeping.

Figure 1:
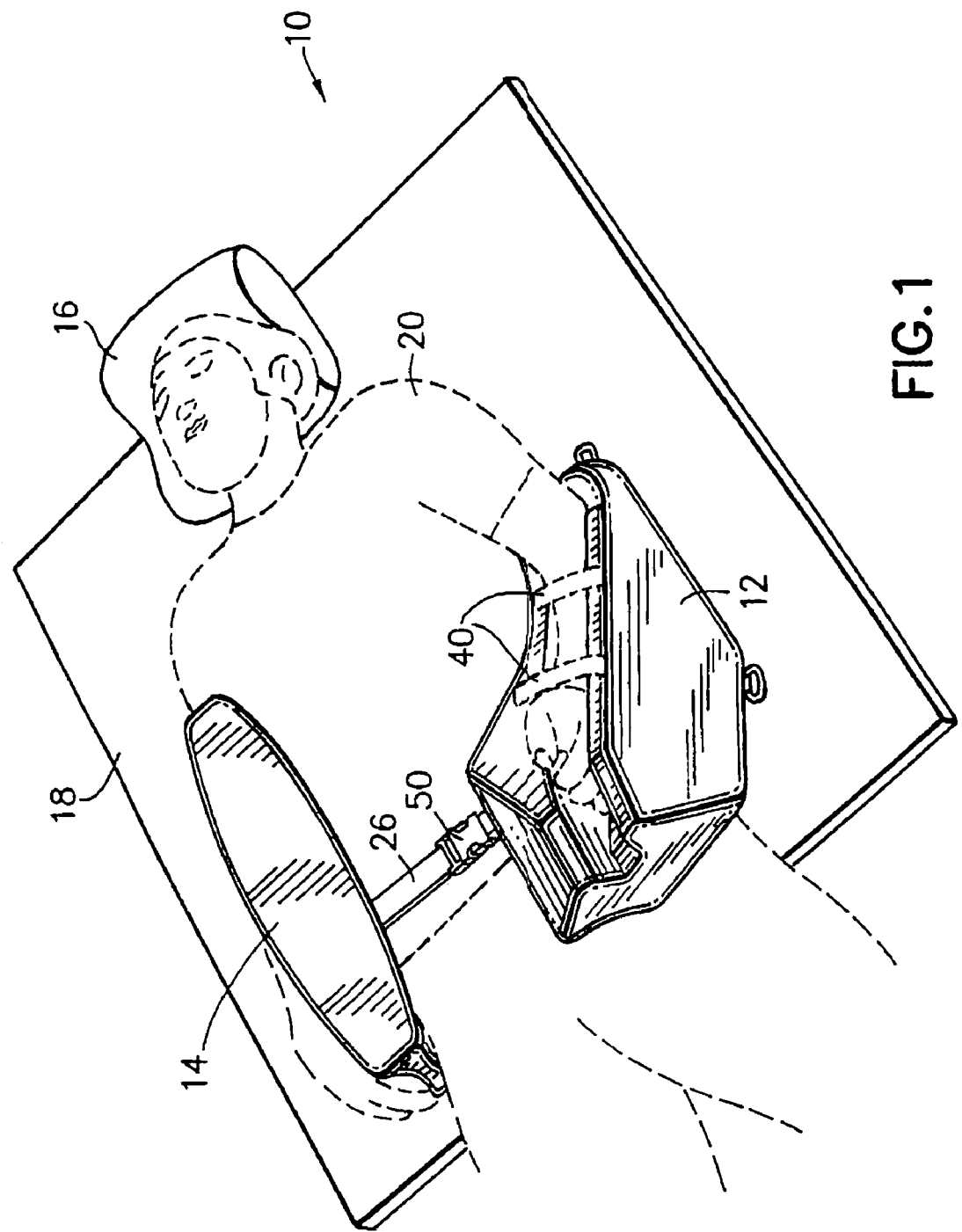
FIG. 1 shows an example embodiment of a support system in accordance with the present invention.
Figure 2:
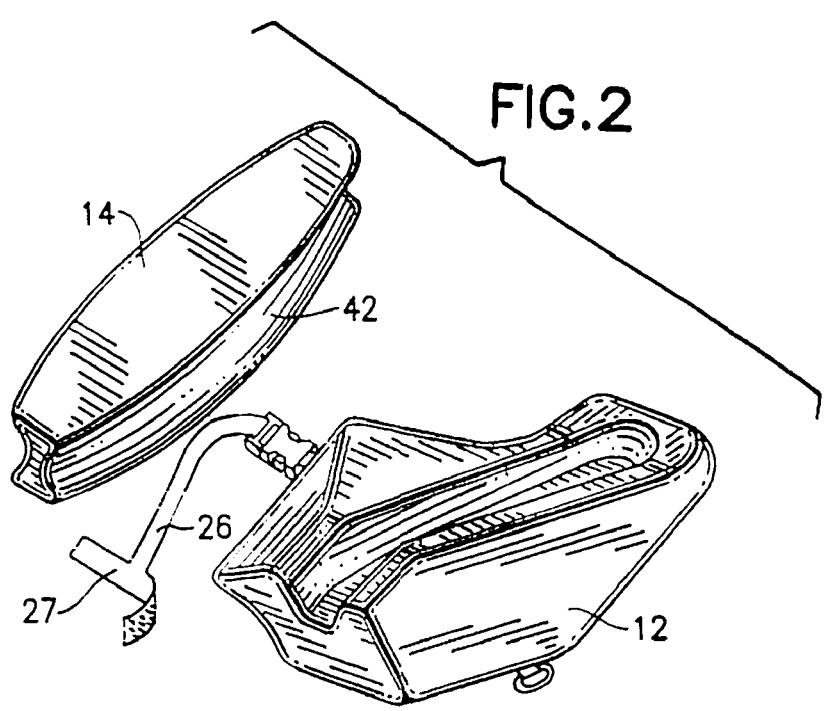
FIG. 2 shows a perspective view of example embodiments of an arm cradle and side bolster in accordance with the present invention.
Figure 4:
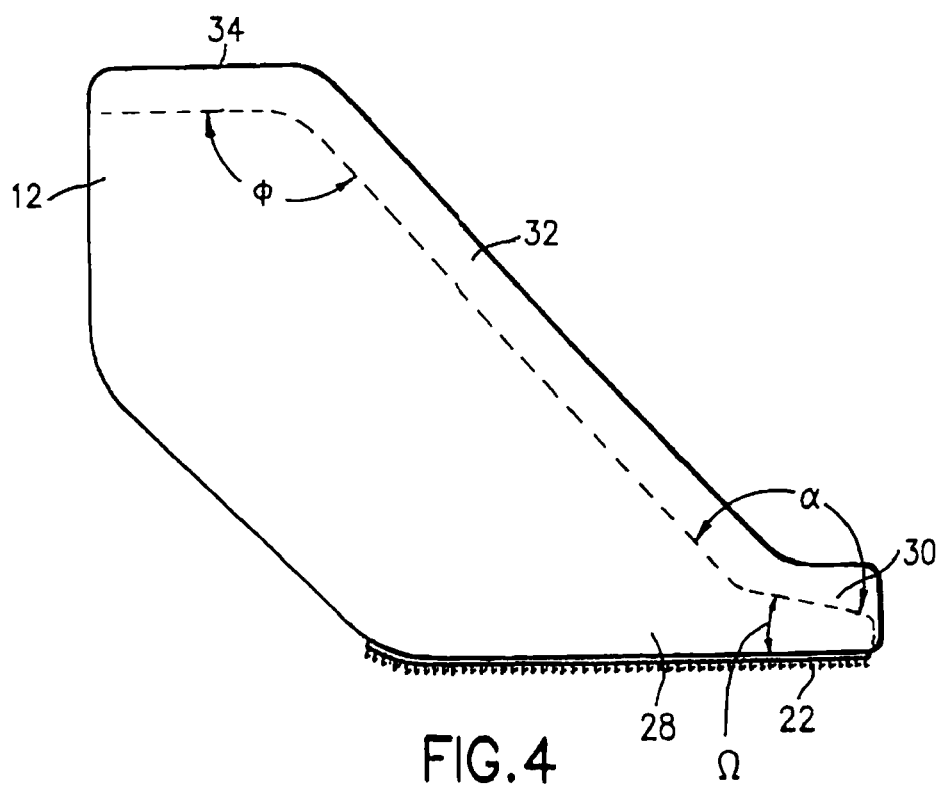
FIG. 4 shows a side view of an example embodiment of an arm cradle in accordance with the present invention.

As shown in FIG. 1, the support system 10 may comprise four portions, including an arm cradle 12, a side bolster 14, an optional head support 16, and an optional mat 18. FIG. 2 shows a perspective view of the arm cradle 12 and side bolster 14. FIG. 4 shows a side view of the arm cradle 12. FIG. 5 shows a top plan view of the arm cradle 12. FIG. 6 shows a top plan view of the side bolster 14. FIG. 7 shows a front elevational view of the side bolster 14.

As can be seen from the Figures, the arm cradle 12 is designed and adapted to hold an arm of a patient at an angle conducive to recovery from shoulder surgery when the patient 20 is in a supine position. The side bolster 14 is designed and adapted to conform to a side of a patient's body and to be positioned against a side of the patient opposite the side of the arm cradle 12 (e.g., with the patient 20 situated between the arm cradle 12 and the bolster 14 as shown in FIG. 1). The optional head support 16 is designed and adapted to conform to the back of a patient's head so as to support the head when the patient 20 is in the supine position. The arm cradle 12, side bolster 14, and optional head support 16 may also be adapted to be positioned on and secured to the mat 18 in a temporary manner.

For example, the arm cradle 12, side bolster 14, and optional head support 16 may all include a bottom portion covered, at least in part, by a Velcro® type material (e.g., a hook and loop type fastener) adapted to interlock with a corresponding material provided on at least corresponding sections of a surface of the mat 18. FIG. 4 shows Velcro® strips 22 on the bottom of the arm support 12 and FIG. 7 shows Velcro® strips 24 on the bottom of the side bolster 14. Alternatively, the entire mat 18 may be covered with a corresponding Velcro®-like material so that the positioning of arm cradle 12, side bolster 14, and head support 16 can be varied as needed to conform to the patient's body type and comfort requirements. Other means of securing the arm cradle 12, side bolster 14, and head support 16 to the mat 18 may be used as would be apparent to those skilled in the art.

The arm cradle 12 may be made of a resilient foam material having a stable base portion 28. As discussed above, this base portion may be adapted to be temporarily affixed to the optional mat portion (e.g., via Velcro® strips 22). As shown in FIGS. 4 and 5, the arm cradle 12 may also include a first section 30 adapted to accept an upper arm of a patient 20. The first section 30 may be angled slightly with respect to the base portion 28. The angle $\Omega$ between the first section and the base portion may be between 0 and 30 degrees. In one embodiment, the angle $\Omega$ between the first section and the base portion may be adjustable. The arm cradle 12 may also include a second section 32 adapted to accept a lower arm of the patient 20. This second section 32 may be at an angle $\alpha$ with respect to the first section 30, in order to support the patient's arm with a bend in the elbow. The angle $\alpha$ of the second section 32 with respect to the first section 30 may be between 90 to 170 degrees. In one example embodiment, the angle $\alpha$ between the second section 32 and the first section 30 may be adjustable. The arm cradle 12 may also include a third section 34 adapted to support a hand of the patient 20. This third section 34 may be at an angle $\phi$ to the second section 32. For example, the angle $\phi$ may be between approximately 120 to 150 degrees, and may be adjustable within this range. The angles may be set depending on the nature of the surgery performed, the optimal recovery position, the patient's unique physiology, patient comfort, or the like. The first, second, and third sections 30, 32, and 34 may be concave and/or contoured to accept the corresponding upper arm, lower arm, and hand of the patient 20.

The arm cradle 12 is adapted to hold the arm and shoulder of the patient 20 in a comfortable and secure position during sleep in a supine position. Straps 40 may be provided to secure the arm in the arm cradle 12.

The side bolster 14 may also be made of a resilient foam material. As discussed above, a bottom portion of the side bolster 14 may be adapted to be temporarily secured to the optional mat 18 (e.g., via Velcro® strips 24). The side bolster 14 may comprise an elongated piece of foam material with a first side 42 adapted to be positioned against the side of the patient's body opposite the side of the body having the surgically repaired shoulder. A second side 44 of the side bolster 14 may be adapted to conform to an extended arm of the patient. The first and second sides 42, 44 may be concave, as shown in FIG. 7. The first and second sides 42, 44 may be identical, enabling use on either side of the patient. The side bolster 14 prevents a post-surgical patient 20 from rolling over during sleep, which could potentially damage the surgically repaired shoulder.

A T-shaped belt or strap 26 may also be provided, which is adapted to be secure the arm cradle 12 to the mat 18 and the patient during sleep. One end of the T-strap may attach to a portion of the arm cradle 12 near the third section 34, e.g., via buckle 50 or a Velcro® connection. The buckle 50 may be attached to the arm cradle 12 via a short length of strap as shown in the Figures, or alternatively buckle 50 be secured directly to the arm cradle 12. A first length of the strap 26 may encircle the patient's waist with a second length (T-portion 27 shown in FIG. 2) secured to the mat 18 via Velcro® or similar material. The second length 27 is attached to the first length perpendicular to the first length of strap 26.

Figure 3:
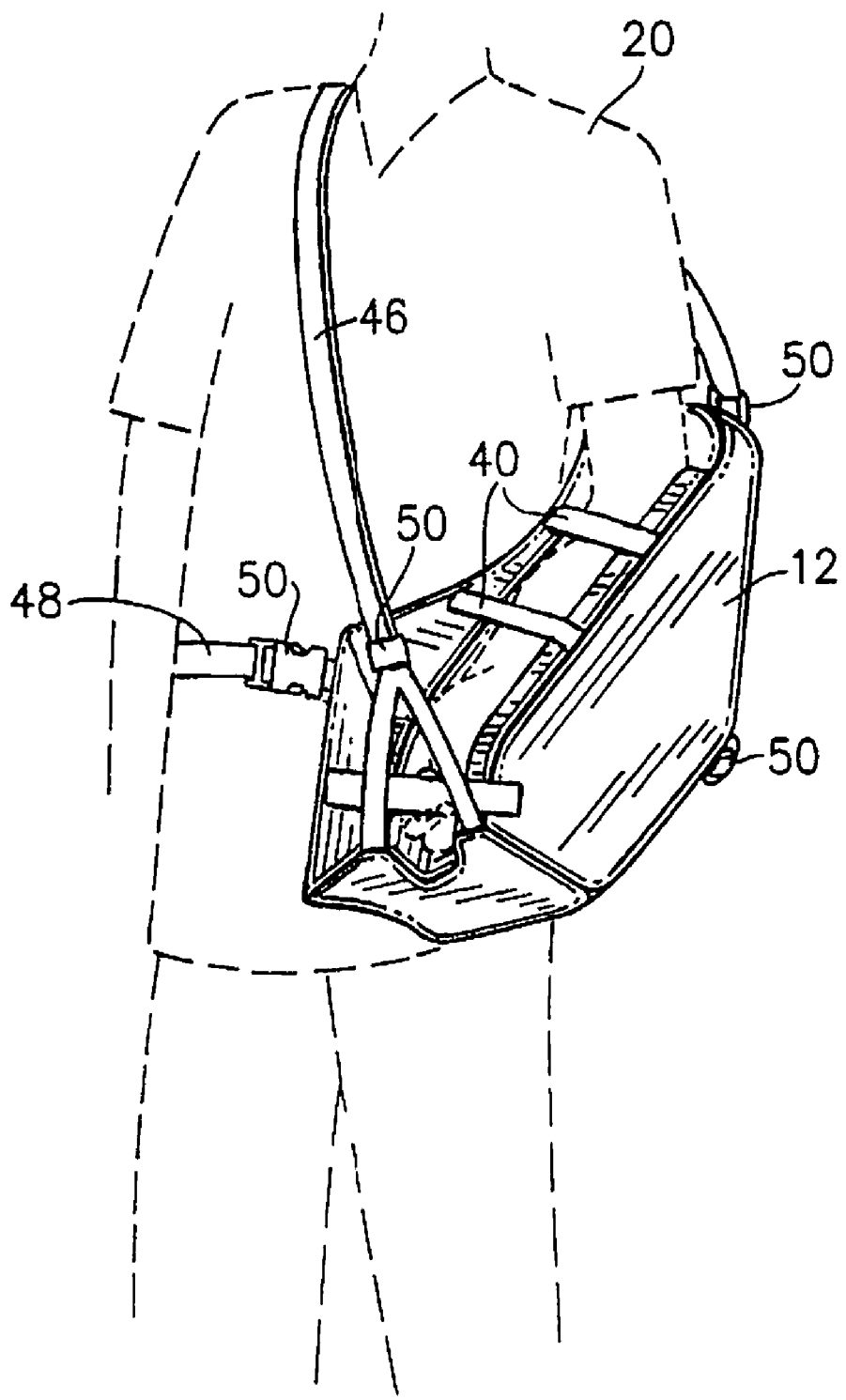
FIG. 3 shows an example embodiment of an arm cradle worn as a sling in accordance with the present invention.

The arm cradle 12 may also be adapted to be worn as a sling during waking hours, as shown in FIG. 3. For example, the T-strap may be used to secure the arm cradle 12 to the patient when used as a sling (e.g., the ends of T-portion 27 may be secured to additional buckles 50 on the arm cradle 12. Alternatively, the arm cradle 12 may include additional straps 46, 48 and buckles 50 which can be configured so as to secure the arm cradle 12 to the patient 20 enabling the arm cradle 12 to be worn as a sling. For example, strap 46 may comprise a shoulder strap that is affixed to the front and rear of the arm cradle 12, and the strap 48 may encircle the patient's waist and be affixed to the arm cradle at buckles 50 as shown in FIG. 7. The strap 48 may be connected to the arm cradle 12 at the same buckle 50 used to connect the T-strap 26. Thus, the arm cradle 12 may be secured to the mat 18 and used to stabilize the patient's arm during sleep as discussed above, and then, due to the temporary Velcro® type attachment, removed from the mat 18 and worn as a sling during waking hours. Advantageously, the patient 20 can move from sleeping in bed to walking around without the need to remove the arm from the arm cradle 12, maintaining immobility of the injured arm/shoulder during this process. Such immobility during the surgical recovery process is advantageous, especially in the early stages of recovery immediately following surgery.

It should be appreciated that all straps (including the T-strap 26, T-strap portion 27, shoulder strap 46, and waist strap 48) may be adjustable to fit different patient sizes and to provide for variable positioning of the arm cradle 12. Also, those skilled in the art will appreciate that the configuration, location, and number of different straps and buckles may be provided and are within the scope of the invention.

The optional head support 16 may also be made of a resilient foam material. As shown in FIG. 8, the head support 16 may have a concave top surface adapted to accept the back of the patient's head. Those skilled in the art will appreciate that any type of head support or standard pillow may be used in place of the optional head support 16 to the same effect.

The support system 10 may be provided in different sizes to conform to different body types and sizes. For example, the cradle, bolster, optional mat and optional head support may be provided in one or more of small, medium, large, extra large, and double extra large sizes. The system components may further be provided in separate small, medium, large, extra large, and double extra large sizes for men and women. For example, the different sizes may be scaled versions of the same components (e.g., a small size may include all components scaled to be 20% smaller than a large size). Typical dimensions for large size system components may include an arm cradle 12 in which the first, second and third sections 30, 32, and 34 measure approximately 42 cm overall, a side bolster 14 that may be approximately 48 cm, and a mat 18 that may be approximately 80×60 cm.

It should now be appreciated that the present invention provides an advantageous systems, apparatus, and methods for supporting a patient's arm enabling shoulder surgery patients to sleep in a reclined position in a stable manner and which includes a portion adapted to be worn as a sling during waking hours.

Although the invention has been described in connection with various illustrated embodiments, numerous modifications and adaptations may be made thereto without departing from the spirit and scope of the invention as set forth in the claims.

What is claimed is:

1. A support system for surgical patients, comprising:
    an arm cradle adapted to hold a first arm of a patient at an angle when the patient is in a supine position, the arm cradle comprising a first section adapted to accept an upper arm of the patient, a second section adapted to accept a lower arm of the patient, and a base portion; and
    a side bolster with a first side adapted to be positioned against a side of the patient opposite the arm cradle, the side bolster adapted to stabilize the patient in the supine position;
    wherein:
        the first section has a first slope defined by a first angle with respect the base portion and the second section has a second slope defined by a second angle with respect to the first section such that both the first and second sections extend along a plane that is perpendicular to a bottom of the base portion.

2. A support system in accordance with claim 1, further comprising:
    a mat;
    wherein the arm cradle and the side bolster are temporarily secured to the mat.

3. A support system in accordance with claim 2, further comprising:
    a T-shaped strap for securing the arm cradle to the mat and the patient.

4. A support system in accordance with claim 3, wherein the T-shaped strap comprises:
    a first end adapted to be secured to the arm cradle;
    a first length of strap for encircling a waist of the patient; and
    a second length of strap adapted to be secured to the mat which is attached to the first length and perpendicular to the first length.

5. A support system in accordance with claim 1, further comprising a head support secured to the mat and adapted to support a head of the patient.

6. A support system in accordance with claim 1, wherein:
    the first angle is in a first range between 0 and 30 degrees with respect to the base portion; and the second angle is in a second range between 90 and 170 degrees with respect the first section.

7. A support system in accordance with claim 1, wherein the arm cradle further comprises:
    a third section adapted to support a hand of the patient.

8. A support system in accordance with claim 7, wherein:
    the third section is angled with respect to the second section.

9. A support system in accordance with claim 8, wherein:
    the third section is at an angle in a third range between 120 and 150 degrees with respect to the second section.

10. A support system in accordance with claim 1, further comprising:
    one or more straps fixed to the arm cradle for securing the first arm of the patient in the arm cradle.

11. A support system in accordance with claim 1, wherein the arm cradle is adapted to be worn as a sling when the patient is ambulatory.

12. A support system in accordance with claim 11, further comprising:

one or more straps affixed to the arm cradle configured to support the arm cradle for use as a sling.

13. A support system in accordance with claim 12, wherein:
the one or more straps comprise a shoulder strap and a waist strap.

14. A support system in accordance with claim 12, wherein:
the one or more straps are adapted to secure the arm cradle to the mat when the patient is in the supine position.

15. A support system in accordance with claim 1, wherein the side bolster has a second side adapted to conform to a second arm of the patient in an extension position.

16. A support system in accordance with claim 1, wherein the side bolster has a second side which is symmetrical with the first side, enabling use of the side bolster on either side of the patient.

17. A support system in accordance with claim 16, wherein at least portions of the first side and the second side of the side bolster are concave.

18. A support system in accordance with claim 1, wherein:
the patient comprises a shoulder surgery patient; and
the angle at which the arm cradle holds the first arm of the patient in the supine position is chosen so as to speed recovery from the shoulder surgery while immobilizing the shoulder during sleep.

19. A convertible support for shoulder surgery patients, comprising:
an arm cradle adapted to hold an arm of a patient at an angle when the patient is in a supine position and adapted to be worn as a sling when the patient is ambulatory, the arm cradle comprising a first section adapted to accept an upper arm of the patient, a second section adapted to accept a lower arm of the patient, and a base portion; and
straps affixed to the arm cradle configured to support the sling when the patient is ambulatory;
wherein:
the first section has a first slope defined by a first angle with respect the base portion and the second section has a second slope defined by a second angle with respect to the first section such that both the first and second sections extend along a plane that is perpendicular to a bottom of the base portion.

20. A method for providing a convertible support for shoulder surgery patients, comprising:
providing an arm cradle adapted to hold a first arm of a patient at an angle when the patient is in a supine position and adapted to be worn as a sling when the patient is ambulatory, the arm cradle comprising a first section adapted to accept an upper arm of the patient, a second section adapted to accept a lower arm of the patient, and a base portion; and
providing straps affixed to the arm cradle configured to support the sling when the patient is ambulatory;
wherein:
the first section has a first slope defined by a first angle with respect the base portion and the second section has a second slope defined by a second angle with respect to the first section such that both the first and second sections extend along a plane that is perpendicular to a bottom of the base portion.

21. A method in accordance with claim 20, further comprising:
providing a side bolster with a first side adapted to be positioned against a side of the patient opposite the arm cradle, the side bolster adapted to stabilize the patient in the supine position.

* * * * *